United States Patent [19]
Alberici et al.

[11] Patent Number: 5,084,908
[45] Date of Patent: Jan. 28, 1992

[54] TOMOGRAPHIC SYSTEM

[75] Inventors: Peter Alberici, Turnersville, N.J.; Henry J. Tancredi, Gwynedd, Pa.

[73] Assignee: Incubation Industries, Ivyland, Pa.

[21] Appl. No.: 475,485

[22] Filed: Feb. 7, 1990

[51] Int. Cl.$^5$ ............................................. G01N 23/04
[52] U.S. Cl. ........................................ 378/4; 378/20; 378/108
[58] Field of Search .................. 378/4, 20, 108–112, 378/145–146, 205, 8, 96, 97, 99

[56] References Cited

U.S. PATENT DOCUMENTS

| | | | |
|---|---|---|---|
| 4,032,784 | 6/1977 | Rich | 378/112 |
| 4,595,949 | 6/1986 | Funster et al. | 378/110 |
| 4,624,007 | 11/1986 | Murenushi | 378/20 |
| 4,649,555 | 3/1987 | Matsubayeshi | 378/20 |

Primary Examiner—Carolyn E. Fields
Assistant Examiner—David P. Porta
Attorney, Agent, or Firm—William H. Murray; Frank M. Linguiti

[57] ABSTRACT

A system for obtaining a tomographic image of an object having a plurality of candidate object image locations is provided. The system includes a processor containing object density information as well as a source of radiation energy for irradiating the object wherein the source of radiation is under the control of the processor. A radiograph of the object is provided and applied to a digitizer for indicating a selected object image location on the radiograph and transmitting the selected location to the processor. The processor then controls the source of radiation to adjust the level of radiation in accordance with the transmitted location and the stored object density information. The processor also controls a translator to adjust the relative object to equipment position in accordance with the transmitted location signal. The source of radiation energy can be moved through pluridimensional patterns.

13 Claims, 6 Drawing Sheets

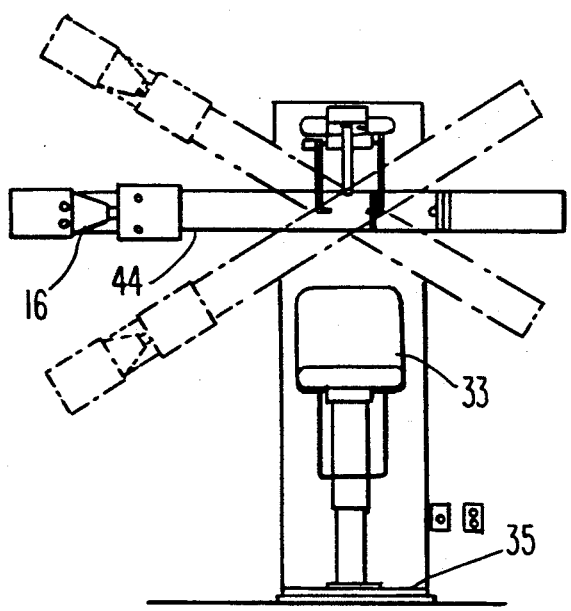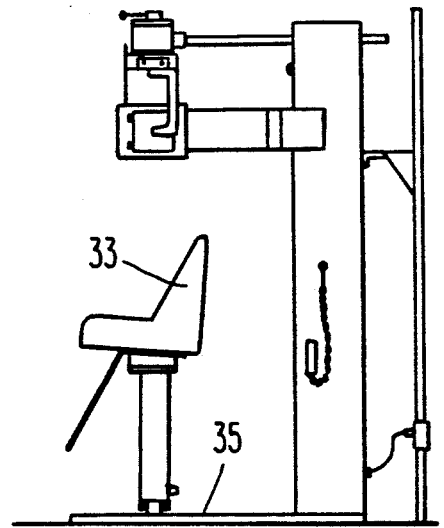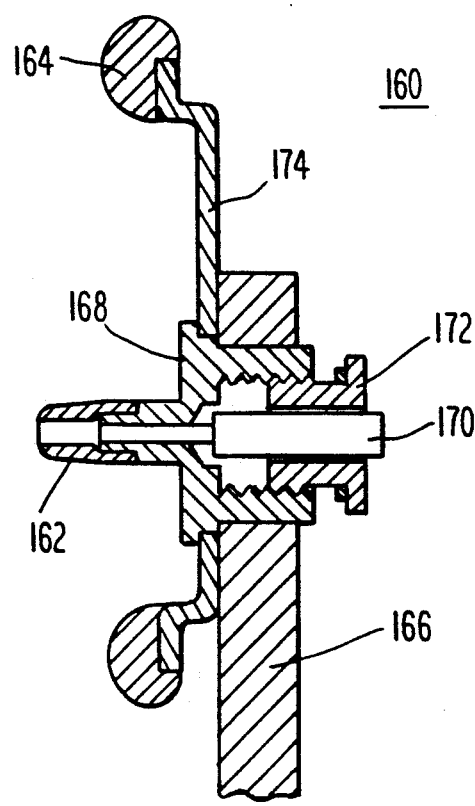

TOMOGRAPHIC SYSTEM

BACKGROUND OF THE INVENTION

1. Field of the Invention.

The subject invention relates generally to computerized tomography, and more particularly to an improved system for providing tomographic images of subject wherein a computerized tomographic system is controlled in accordance with object density information and digitized mapping information determined from a preliminary image of the subject.

2. Prior Art.

In this field it is desirable to obtain radiographic images of controlled depth and slice thickness for accurate diagnostic purposes. In performing tomographic imaging of objects, it is desirable to avoid repeated irradiation of the object. However, obtaining the correct positioning and the correct exposure levels for tomographic studies frequently required making repeated exposures of the object in order to iteratively correct the positioning and the exposure level. This method required exposing the object to a radiation dose which is relatively high.

A conventional X-ray computerized-tomographic apparatus could display both a preliminary image such as a scanogram as well as a tomographic image. Thus, before acquisition of the tomographic images of the target portion of the object under examination, the scanogram, which covered a wide region including the diseased portion, was produced. The scanogram was based upon an X-ray transmission detection signal. By observing the scanogram, positions for imaginary slices of the subject for which the tomographic images were to be obtained were determined. The tomographic images were obtained by reconstructing other detection signals based upon the determined slice positions.

In systems such as this, a control device controlled motors for the translatory displacement of the carrier in the horizontal plane so that the pivoting axis of the carrier followed a curve which at least substantially corresponded to the shape of the subject. The drive motor for the carrier pivots the carrier so that the connecting line between the focal spot of the radiation source and a slit diaphragm of the film holder through which the radiation is incident upon the film extends approximately perpendicularly with respect to the curve. The film is transported within the film holder at a velocity which is proportional to and higher than the translation velocity of the carrier. Alternately, the subject may be held stationary and only the portions of the tomographic system translated.

However, inaccuracies and, hence unsharpness and distortion may still occur. Schrieber, U.S. Pat. No. 4,418,419 issued on Nov. 29, 1983, teaches a solution to this problem wherein a control device included an element which was applied to the subject. The control device also included an arithmetic unit for calculating control signals for the drive motor. A tomographic system was then controlled in accordance with the control signals from the control device. However, this control device added considerable expense and still did not achieve correct exposures at all points of the translation of the system.

It is also known to provide computerized tomographic systems wherein a patient was subjected to a scanographic scanning operation prior to the computer tomograph scanning operation, to specify or determine a tomographic scanning portion for a displayed X-ray image. For the preliminary scanning operation, an X-ray tube and an X-ray detector array of the X-ray CT apparatus, were arranged in a fixed position and the patient translated along a longitudinal axis between the X-ray tube and the X-ray detector. However, this method often required undesirably high levels of irradiation of the subject and movement of the subject may result in less precise placement of the subject with respect to the tomographic system.

In the prior art the scanogram was displayed on a CRT apparatus and lines through the image were arranged. After seeing the scanogram, an operator specified tomographic scanning portions and pressed the keys of a keyboard to indicate where in the object the scan slice should be taken. Automatic positioning of the source of X-ray irradiation of the object for CT scanning on the specified portions of the scanographic image in a predetermined order could then proceed. Such a system is taught in U.S. Pat. No. 4,649,555, issued to Matsubayashi on Mar. 10, 1989. However, the system of Matsubayashi still did not provide correct exposures for the different possible studies of selected locations of the object, thereby often requiring extra irradiation of the object.

The most common solution to this problem was to have an operator make a series of measurements of the subject in accordance with the scanographic image. A series of complex, trigonometric, geometric, and arithmetic operations based on the measurements were performed by the operator to determined the remaining information required for correct exposure once the tomographic system was properly positioned around the subject. Performance of these operations required a highly trained operator and were still subject to error. When errors were made, the exposures were incorrect and additional irradiation of the subject was required at a corrected level of irradiation.

Such earlier methods required that certain anatomical structures be identified from the radiographic image, previously made of the subject. The physical dimensions were determined from this image using manual drawing aids, such as rulers, protractor, and straightedge in order to calculate the required relative subject to X-ray position. This required a working knowledge of trigonometry as well as special training for the operator of the X-ray equipment to determine the patient to equipment relationship. Usually, the first attempt resulted in missed tomographs or at best images that were incorrectly exposed thereby subjecting the patient to undesirable additional radiation and the inconvenience of repeated lengthy and costly procedures.

SUMMARY OF THE INVENTION

A system for obtaining a tomographic image of an object having a plurality of candidate object image locations is provided. The system includes a processor containing object density information as well as a source of radiation energy for irradiating the object wherein the source of radiation is under the control of the processor. A radiograph of the object is provided and applied to a digitizer for indicating a selected object image location on the radiograph and transmitting the selected location to the processor. The processor then controls the source of radiation to adjust the level of radiation in accordance with the transmitted location and the stored object density information.

BRIEF DESCRIPTION OF THE DRAWINGS

FIGS. 3A, 3B show front and side views of the system of the present invention, FIG. 7 shows the headholder of the tomographic system of FIG. 1.

DETAILED DESCRIPTION OF THE INVENTION

Figure 1A:
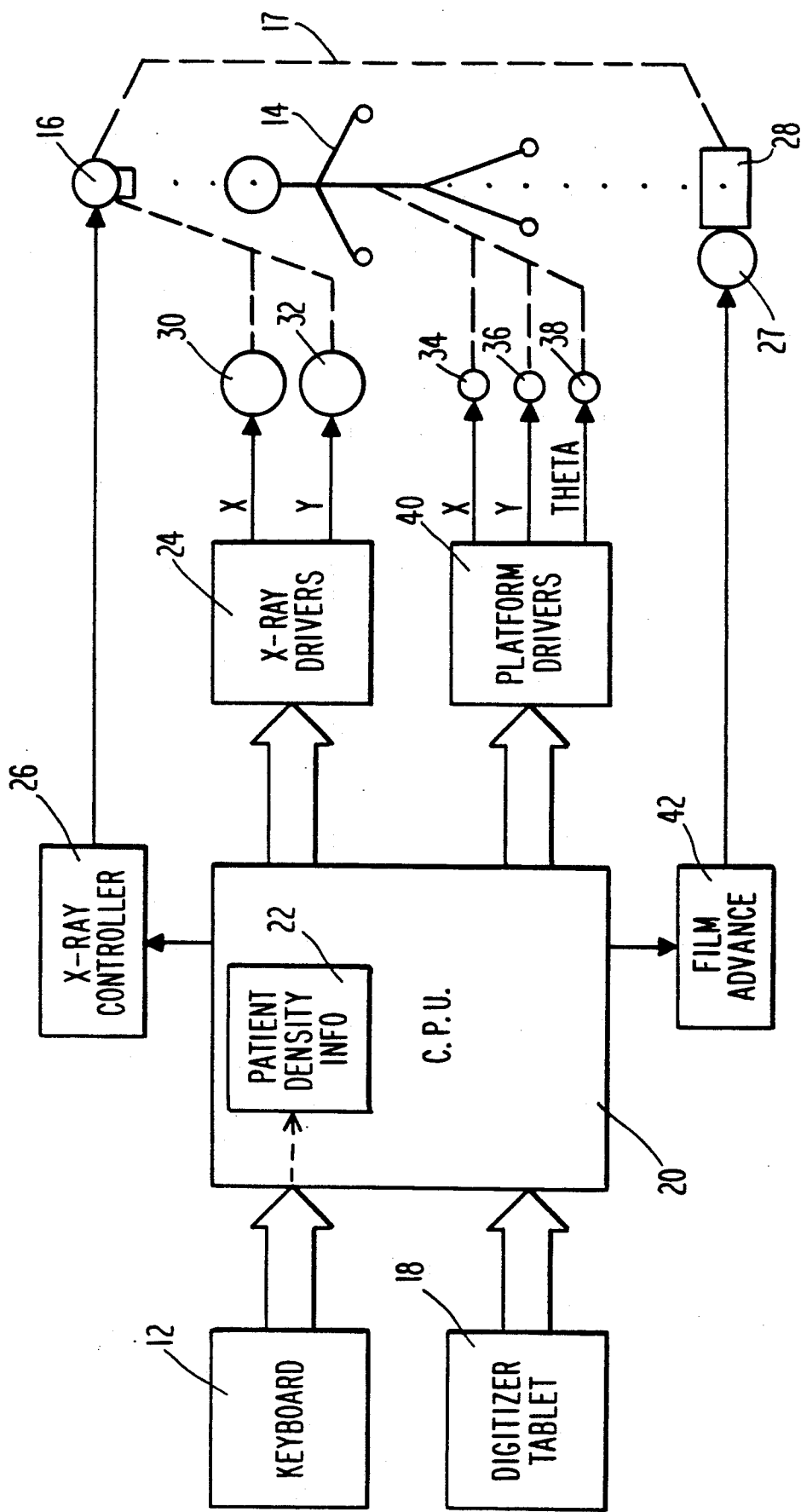
FIGS. 1A, 1B show a block diagram representation of the improved tomographic system of the present invention, and a stylus for indicating a location on the digitizer of the system.
Figure 1B:
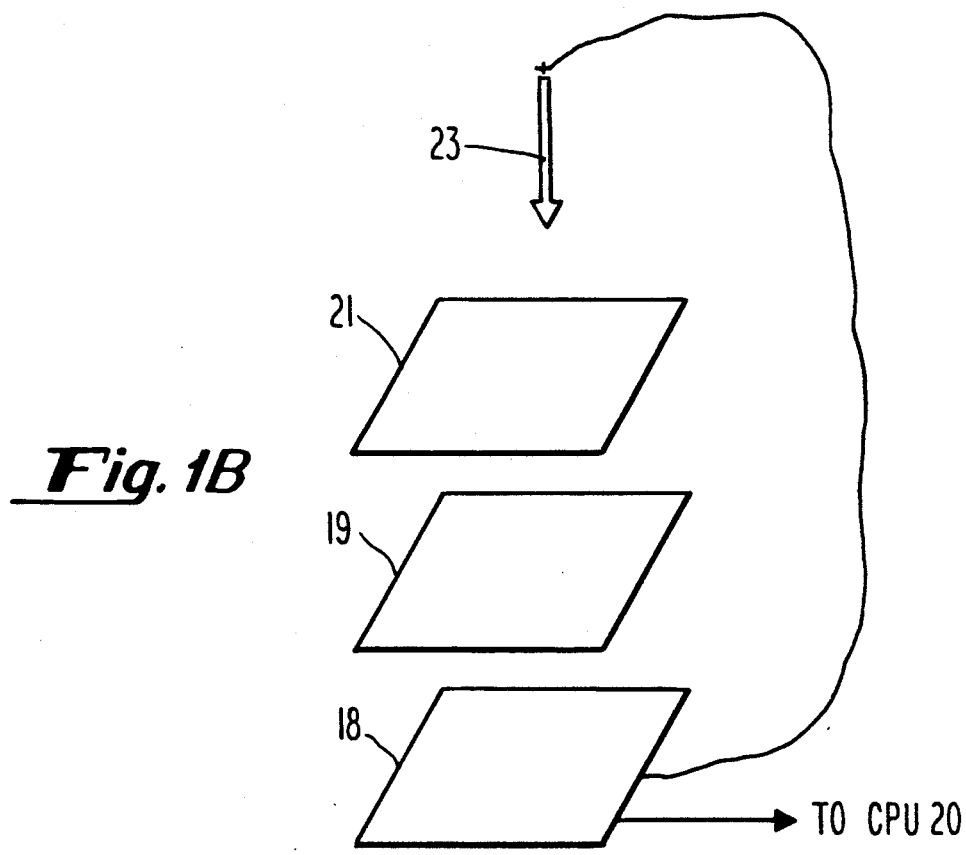
Figure 2:
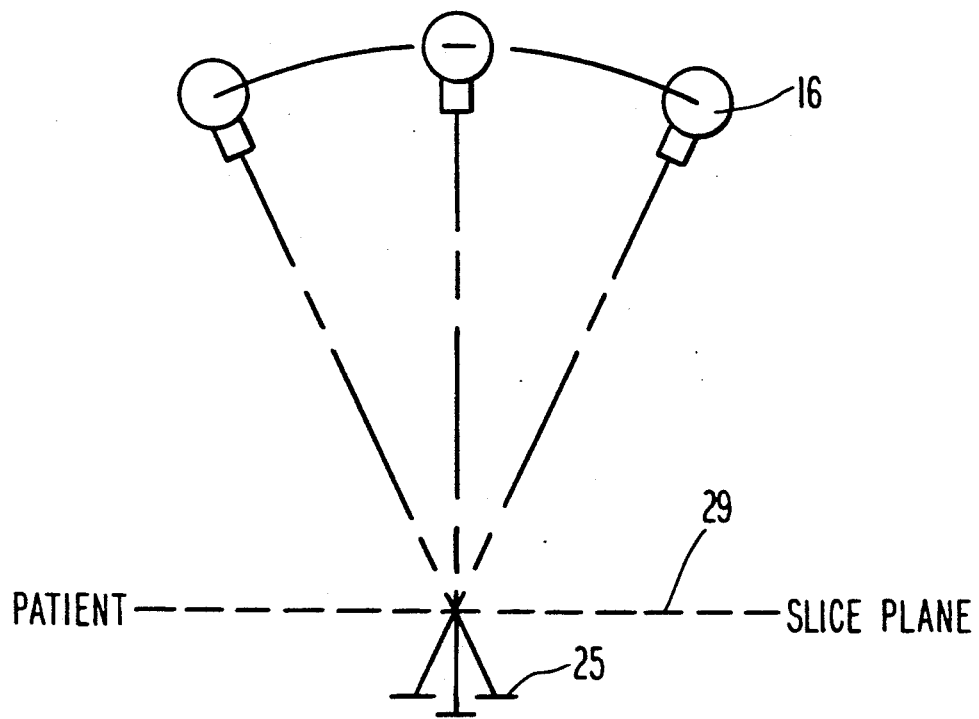
FIG. 2 shows an example of relative motion between the X-ray tube of the system of FIG. 1 and a slice plane.

Referring now to FIGS. 1A, 1B and 2 there is shown improved computerized X-ray tomographic system 10 and stylus 23 of improved computerized X-ray tomographic system 10. In computerized X-ray tomographic system 10, an operator selects a type of computerized tomographic study using keyboard 12 and prompts are provided to the operator by CPU 20 to assist in performing the selected study. In a typical study, CPU 21 instructs the operator of tomographic system 10 to generate radiograph 21 of subject 14 using radiation from radiation source 16 or X-ray tube 16. The Radiograph 21 generated by the operator in response to the prompt is selected to display portions of subject 14 including a plurality of candidate subject image locations on subject 14. Candidate subject image locations are locations on subject 14 which the operator of X-ray tomographic system 10 may select to be the location of a scan study by X-ray tomographic system 10.

Radiograph 21 of subject 14 showing the candidate subject image locations is placed on illuminator 19 of digitizer tablet 18 by the operator. Stylus 23 is provided for indicating, in accordance with radiograph 21, which of the candidate image locations is selected by the operator to be the actual location of the study performed on tomographic system 10. Radiograph 21 thus serves as a map for mapping locations of the image of subject 14 onto digitizer tablet 18.

Digitizer tablet 18 contains sensors and circuitry for detecting the location on radiograph 21 indicated by the operator using stylus 23 and transmits digitized location information with respect to the selected candidate subject image location to CPU 20. CPU 20 then determines the correct subject-to-machine position for the selected study and the correct level of X-ray radiation from X-ray tube 16, in accordance with the digitized location information from digitizer tablet 18 and patient density information 22. CPU 20 then controls the positioning of X-ray tube 16 by way of X-ray drivers 24 as well as the level of radiation energy, by way of X-ray controller 26 to expose an image of subject 14 on film 25 within film cassette 28. Patient density information 22 is entered into CPU 20 by way of keyboard 12.

CPU 20 controls the positioning of X-ray tube 16 by way of tube motors 30, 32 which are under the control of X-ray drivers 24. X-ray drivers 24 control in both the X dimension and the Y dimension and therefore may provide pluridimensional scanning of subject 14 by movement of X-ray tube 16. The movement of X-ray tube 16 under the control of CPU 20 includes rectilinear, circular, elliptical, and hypocycloidal motion as well as angle of swing. The axial scans performed by X-ray tomographic system 10 are distinguished from the radial scans of a CAT scanner. X-ray tube 16 is mechanically coupled to film cassette 28 by linkage 17 to control relative movement. Platform motors 34, 36, 38 position subject 14 by translating and rotating chair 33 on platform 35 in which subject 14 sits during a study performed using tomographic system 10.

Referring now to FIGS. 3A, 3B, CPU 20 controls the positioning of subject 14 by way of platform motors 34, 36, 38 which are under the control of platform drivers 40. Platform drivers 40 may control platform motors 34, 36 to move platform 35 to selected Cartesian coordinates within a horizontal plane. Additionally, platform motor 38 rotates subject 14 when subject 14 is positioned at the selected Cartesian coordinates.

Figure 4:
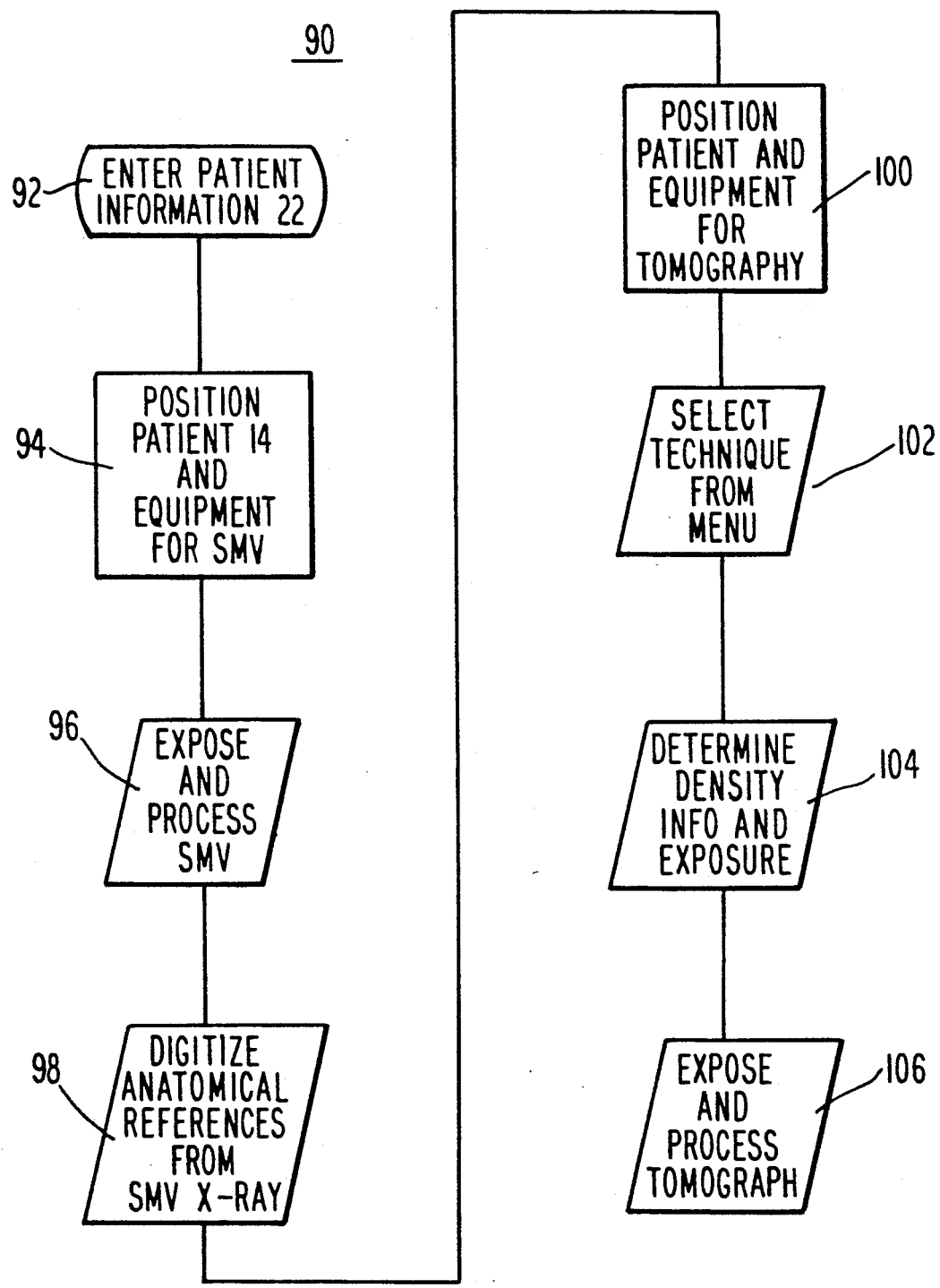
FIG. 4 shows a flow chart representation of a tomographic study done using the system of FIG. 1.

Referring now to FIG. 4, there is shown algorithm 90 for performing an operation using system 10 of the present invention. A typical operation for improved tomographic system 10 is a study of a temporomandibular joint (not shown). In this operation the operator enters patient density information 22 as shown in block 92. This information includes data that determines the X-ray exposure, such as age, sex, race and physique. This data is converted to mathematical coefficients within CPU 20 which alter the normal default exposure values to corrected exposure values prior to the actual exposure event in accordance with the entered patient data. Additionally, certain patient information may later be used for the radiograph identification imprint. Entry of patient density information 22 into CPU 20 of tomographic system 10 is made by way of keyboard 12.

In the temporomandibular joint example, a submentovertex image is prompted by CPU 20. Thus, the operator selects, by means of menu selection, a submentovertex image study before proceeding with the tomographic imaging. When the operator selects the submentovertex procedure, patient platform 35 is driven to a predetermined position within tomographic system 10 under the control of platform driver 40 as shown in block 94. Additionally, X-ray tube 16 is driven to the position required for the submentovertex image of subject 14 under the control of X-ray drivers 24. The operator places subject 14 on patient platform 35 and secures the head of subject 14 using a headholding mechanism with the head of subject 14 tilted to the proper X-ray axis angle for the submentovertex image.

CPU 20 then provides another prompt to the operator of improved tomographic system 10. The next prompt is for a submentovertex exposure as shown in block 96. For safety reasons, this exposure requires that a "dead-man" switch be depressed and held throughout the exposure in addition to the keyboard exposure switch.

After exposure of the film in film cassette 28 and its processing, the developed film is placed on illuminator 19 of digitizer tablet 18. Illuminator 19 is less than one-half inch thick and is disposed over a plurality of one-quarter inch diameter fluorescent tubes (not shown) or flat solid state illuminators (not shown) may be used.

The operator of tomographic system 10 is prompted by CPU 20 to enter certain structures, including anatomical structures, using the tablet stylus as shown in block 98. For the submentovertex image, the structures which are entered include one ear rod for a magnification correction coefficient, an end of the opposing ear rod in order to establish an imaginary base line projecting from one ear canal to the other and also establish a mid-sagittal line. It is the mid-sagittal line from which all angles of patient rotation may be derived. Additionally, cardinal points or extremes and each mandibular condyle are prompted by CPU 20 for the submentovertex study. Approximately seven spots may be required for such a study.

In response to the selection of the required tomographic procedure by way of keyboard 12 and CPU 20, the patient platform 35 is automatically positioned at the proper location for the indicated study and the indicated image location by CPU 20 using platform drivers 40 to control platform motors 34, 36, 38 to move patient platform 35 to the required location. This positioning is set forth in block 100 of algorithm 90. The technique is then selected from the menu as shown in block 92.

CPU 20 then determines, in accordance with the study and image location selected by the user of tomographic system 10, as well as in accordance with patient density information 22, the proper level of radiation energy to be provided by X-ray tube 16 as shown in block 104. X-ray tube 16 is then controlled by CPU 20 using X-ray controller 26 to provide the required level of radiation energy to irradiate subject 14 and perform the study selected. At the end of the exposure by X-ray 16, film cassette 28 is advanced by film advance motor 27 under the control of film advance controller 42 as directed by CPU 20.

X-ray exposure parameters, corrected in accordance with patient density information 22, are applied to exposure control circuits within X-ray controller 26 in order to control the amount of power provided to X-ray tube 16 as shown in block 106. When the exposure is initiated, articulating arm 44 of tomographic system 10 begins a predetermined geometrical motion in accordance with the selected study and other parameters. At the beginning of the geometrical pattern, the X-ray exposure is turned on and remains on until the end of the pattern to provide exposure symmetry. Articulating arm 44 is driven by X-ray motors 30, 32 in a gimbal arrangement. This configuration allows an infinite number of geometric patterns to be executed thereby allowing selection of the most appropriate motion for a selected tomograph procedure. At the end of the exposure film cassette 28 advances to the next image position and patient platform 35 advances to the next slice position in readiness for the next exposure of the study.

Patient placement accuracy is important in order to obtain repeatable images. This accuracy is achieved within computerized tomographic X-ray system 10 by headholder Z that is a line with ear rods to secure patient 14 by clamping the head of patient 14 between ear cushions. Headholder Z is an integral part of the patient platform moving in unison with the platform motion. During installation of X-ray tomographic system 10, headholder is aligned with the central X-ray beam of X-ray tube 16 so that the pivot point is at the intersection of the mid-sagittal and base lines as viewed from a submentovertex projection.

X-ray tomographic system 10 may be provided with various types of safety equipment. For example, interlocks for controlling the beam limiting device and encoding them to the image field size so that operation is halted when the operator is alerted that the wrong beam limiter is in use, as determined by the procedure selected from the menu by means of keyboard 12.

Other interlocks include cassette switches to prevent headholder collision when patient platform 35 is rotated or when the elevation adjustment is running as well as the "deadman" switch previously described. The slice plane thickness is determined by the geometric pattern selected and the differential angle of swing. In theory, the best angles are those in which everything but the structures in the thin slice plane are intentionally blurred keeping in mind that thinner slices result in lower contrast radiographs. In order to maintain image sharpness throughout the entire image plane field, a multi-bar linkage is used between the X-ray tube and the film cassette. This linkage allows the tube to point at the central object plane or fulcrum while keeping the film plane parallel to the object plane regardless of the geometric pattern in use.

Figure 5:
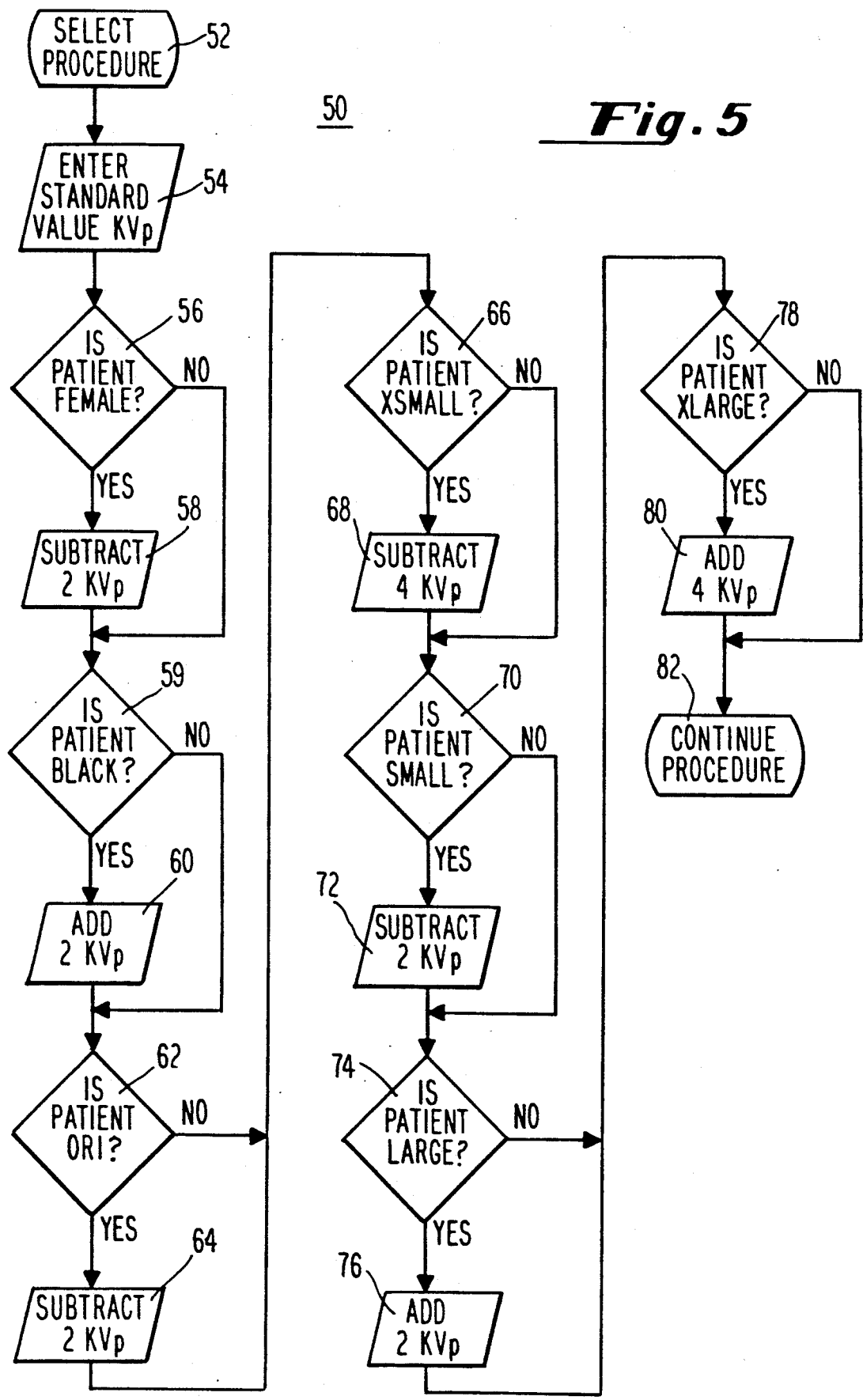
FIG. 5 shows a flow chart representation of the method for altering normal default exposure values according to patient information.

Referring now to FIG. 5, there is shown routine 50 for altering normal default values of radiation level according to the information of patient density information 22. Routine 50 is initiated by the selection of a procedure to be performed by improved X-ray tomographic system 10 as shown in start 52. The standard values of exposure for the study selected in start 52 is called up in block 54. A determination is then made at decision 56 whether patient 14 being studied is male or female. If the patient being studied is female, as determined in decision 56, two kilovolts are subtracted from the standard value kilovolt called up in block 54, as shown in block 58. If patient 14 is male, no adjustment is made to the standard value.

A determination is then made in decision 59 whether patient 14 is Black. If patient 14 is Black, as determined in decision 58, two kilovolts are added to the radiation exposure value as shown in block 60. If patient 14 is not Black, the exposure value is not altered at this point within routine 50.

A determination is then made at decision 62 whether patient 14 is Oriental. If patient 14 is Oriental, two kilovolts are subtracted from the exposure value as shown in block 64. If patient 14 is not Oriental, the value is not modified.

At decision 66, a determination is made whether patient 14 is extra small. If patient 14 is extra small, as determined at decision 66, four kilovolts are subtracted from the exposure value as shown in block 68. If patient 14 is not extra small, the exposure value is not altered. A determination is then made in decision 70 whether patient 14 is small. If patient 14 is small, two kilovolts are subtracted from the exposure value as shown in block 72. If patient 14 is not small, as determined in decision 70, the exposure value is not altered.

At decision 74, a determination is made whether patient 14 is large. If patient 14 is large, as determined at decision 74, two kilovolts are added to the exposure value as shown in block 76. If patient 14 is not large, as determined at decision 74, the exposure value is not altered. At decision 78, a determination is made whether patient 14 is extra large. If patient 14 is extra large, as determined in decision 78, four kilovolts are added to the exposure value as shown in block 80. If patient 14 is not extra large, the exposure value is not altered.

The procedure selected at start 52 is then continued by the operator as shown in terminal 82. For correct execution of routine 50, patient information 22 may contain the sex of the patient, either male or female, the race of the patient, either Caucasian, Black, or Oriental, and the frame size which may be extra small, small, medium, large, and extra large. The standard values accessed in block 54 are based on a male, Caucasian, medium-frame size patient. Thus, for example, a large or an extra-large patient will require an increase in radiation, as shown in blocks 76, 80 in order to increase the X-ray penetration. Likewise, for the other parameters, the anode voltage is adjusted by, for example, subtracting two kilovolts peak for a female, adding two kilovolts peak for a Black, etc.

Figure 6:
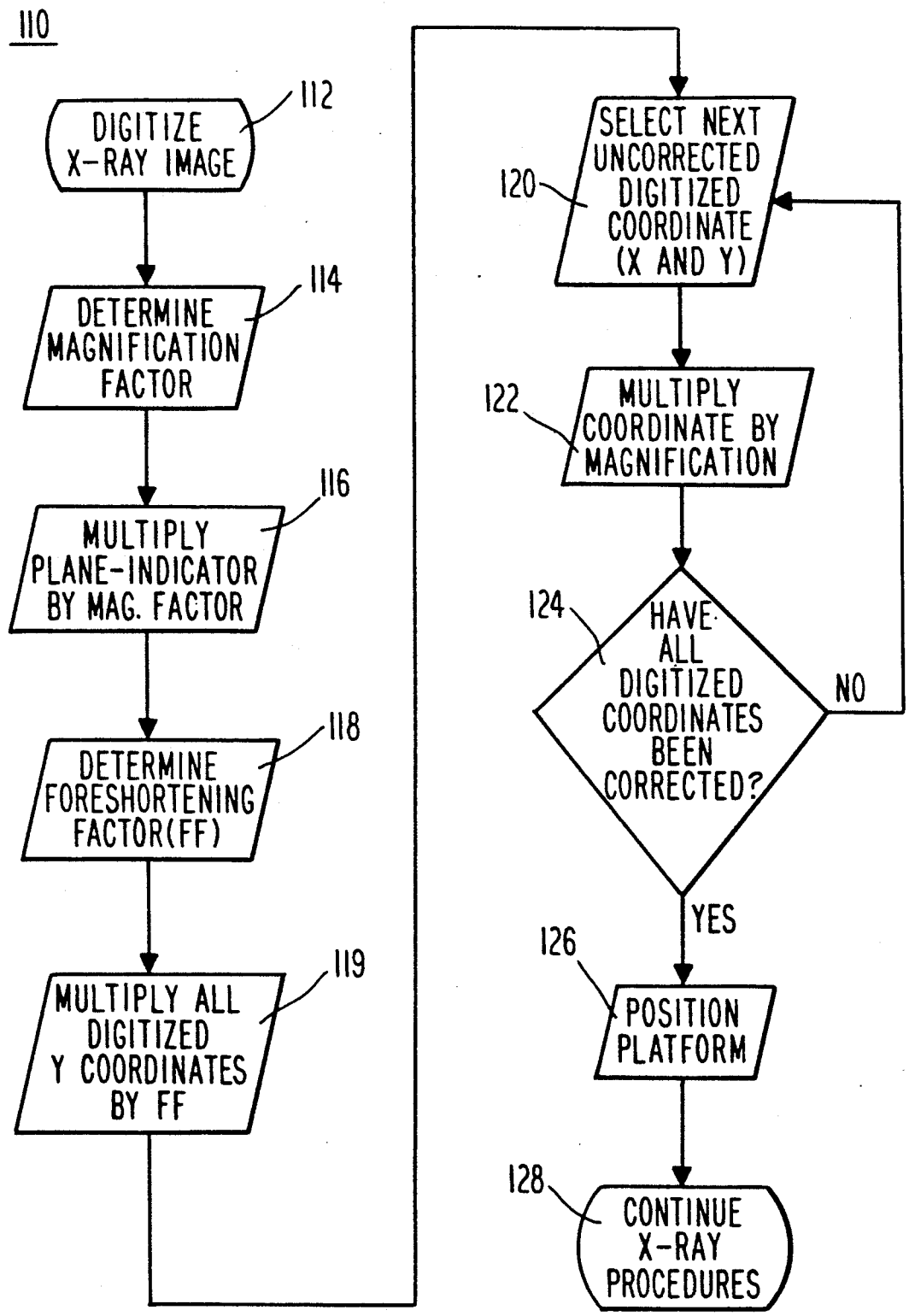
FIG. 6 shows a flow chart representation of a method for correcting location information from the digitizer of FIGS. 1A, 1B.

Referring now to FIG. 6, there is shown a block diagram representation of routine 110 for correcting information from digitizer tablet 18. X-ray imaging of patient 14 when patient 14 is located off of the film plane causes magnification of the image on the film. The greater the distance between patient 14 and film 25, the greater the magnification. In geometric tomography it is necessary to place patient 14 at slice plane 29 which is located at the fulcrum of the source and film planes. It is also desirable to keep patient 14 as close to film 25 as possible for minimum magnification and maximum clarity. This distance is limited by possible interference between patient 25 and film holder 28 which is in constant motion during exposure. In cranial tomography it is usually the shoulder of patient 25 that limits the object 14 to film 25 proximity. To correct for this inevitable flaw, a means to include the amount of magnification error is provided to allow computation of the coordinate corrections required for accurate placement of the person to equipment relationship. This is accomplished by the inclusion of radio-opaque earplugs 170 or metal inserts 170 of known length in mapping image 21 or radiograph 21. Inserts 170 serve several functions. Among these is the primary function which is to establish a base line for a positioning reference. Also, right side or left side identification is made possible using different size or shapes of earplugs 170. Another function is compensating the digitized coordinates from digitizing tablet 18 for magnification error.

In addition to earplugs 170 there is also provided X-ray opaque plane indicator that shows up in mapping image 21. The plane indicator is manually positioned in line with the patient's Frankfort Plane, or eye-to-ear line, which must be parallel to film plane for a distortionless submentovertex image. This may not always be possible due to possible physical limitations of patient 14 in which case plane-indicator 112 appears as a foreshortened object in the image. The digitizing of plane-indicator 152 on digitizing tablet 18 allows CPU 20 to determine whether the image if foreshortened, and to what amount, for distortion correction of the mapped coordinates.

The plane indicator is also used to correct the coordinates of objects that are not on the same horizontal plane as inserts 170. The correction is made whenever the head of patient 14 must be tilted to obtain a perpendicular slice. For example, if a tomograph is to be taken, in a coronal plane, of a mandible of patient 14 which has an angle of n degrees from the Frankfort Plane. When the head of patient 14 is tilted n degrees to allow a perpendicular slice, the slice coordinate changes because the head is rotated about the axis of earplug 110. If the plane-indicator is set to the n degree angle, the error would manifest itself as a foreshortened object which is used by CPU 20 for coordinate error correction.

The method for performing the magnification and tilt error corrections is set forth in routine 110. As previously described, radiograph 19 is digitized at start 112. A magnification factor is determined as shown in block 114. An object of known dimensions positioned in the same plane as the patient is used to determine this magnification factor. Such a known object has the same magnification as the patient since it is in the same plane. For example, two ends of a rod in that plane can be digitized and transmitted to CPU 20. CPU 20 may then apply the magnified length, as determined by the signals received from digitizer tablet 18, to the known length of the rod to provide a correction factor. The plane indicator is then multiplied by the magnification factor as shown in block 116.

The foreshortening factor is thus determined in block 118. This foreshortening factor is applied only in the Y direction and is determined by applying the magnification factor to the measured rod distance. All Y coordinates are then multiplied by the foreshortening factor as shown in block 119.

After correction using the foreshortening factor, the next uncorrected digitized coordinate is selected in block 120 and multiplied by the magnification factor of block 114 as shown in block 122. In this operation both the X and Y coordinates are corrected. At decision 124 a determination has been made whether all digitized coordinates have been corrected. If all digitized coordinates have not been corrected as determined in decision 124, the next uncorrected digitized coordinate is selected as shown in block 120. If all digitized coordinates have been corrected, as determined by decision 124, the platform 35 is positioned as shown in block 126 and the X-ray procedure is continued as shown in terminal 128.

Referring now to FIG. 7, there is shown headholder 160 of the present invention. In the preferred embodiment of system 10, two headholders 170 are provided, one for each side of the head of patient 14. For sanitary reasons headholder 160 is provided with disposable plastic insert 162 for insertion into the ear of patient 14. A removable rubber pad 164 or air cushion 164 is provided for applying pressure to the head of patient 14. Air cushion frame 174 supports air cushion 164. Headholder 160 of system 10 is supported on upright support arm 116 which is registered to platform 35 and rigidly secured for causing headholder 160 to move in unison with platform 35. Earplug non-removable sleeve 168 receives and supports removable earplug 172 of headholder 160.

Within removable earplug 172, headholder 160 is provided with metal insert 170. Metal insert 170 is not X-ray transparent, while the remaining components of headholder 160 are X-ray transparent. Additionally, a small metal sphere, for example a ball bearing, may be mounted in headholder 160. Similar spheres of varying size can be put on the left and right of patient 14 in order to facilitate in identifying the left side and the right side of patient 14.

While this invention has been described with reference to specific, and particularly preferred, embodiments thereof, it is not limited thereto and the appended claims are intended to be construed to encompass not only the specific forms and variance of the invention shown, but to such other forms and variance as may be devised as those skilled in the art without departing from the true spirit and scope of this invention.

We claim:

1. In a system for obtaining a tomographic image of an object having a plurality of candidate object image locations, said system having processing means and exposure means under the control of said processing means, said exposure means having varying levels of radiation energy output for irradiating the object, means to obtain a tomographic image at a selected object image location of said plurality of candidate object image locations, comprising:

means for providing a radiograph of said object, said radiograph containing first object information including said plurality of candidate object image locations of said object, digitizer means having radiograph mapping means for applying said radiograph to said mapping means to map object image locations, including said plurality of candidate object image locations, onto corresponding mapping means locations, means for indicating said selected object image location on said radiograph and transmitting to said processing means a location signal representative of the mapping means location corresponding to the indicated object image location, said processing means containing stored second object information representative of the density of said object at a plurality of locations, said second object information being independent of said first object information, and said processing means having means for controlling said exposure means to adjust the level of radiation energy output in accordance with the transmitted location signal and said stored second object information.

2. The system of claim 1, further comprising translating means under the control of said processing means for adjusting the relative object to equipment position wherein said processing means has means for controlling said translating means to adjust the relative object to equipment position in accordance with the transmitted location signal.

3. The system of claim 2, wherein said processing means includes means for controlling said translating means to provide predetermined pluridimensional patterns of adjustment of relative object to equipment position.

4. The system of claim 2 wherein a plurality of tomographic images are obtained further comprising means for adjusting the level of radiation energy output and the relative object to equipment position separately for each image of said plurality of tomographic images.

5. The system of claim 2, wherein said translating means comprises means for translating the exposure means.

6. The system of claim 5, wherein said means for translating said exposure means comprises means for translating said exposure means in two dimensions.

7. The system of claim 2, wherein said translating means comprises means for translating said object.

8. The system of claim 7, wherein said means for translating said object comprises means for translating said object in two dimensions and means for rotating said object.

9. The system of claim 1, wherein said digitizer means comprises a surface for disposing said radiograph on said surface.

10. In a system for obtaining a tomographic image of an object having a plurality of candidate object image locations, said system having processing means and translating means under the control of said processing means for adjusting the relative object to equipment position, means for obtaining a tomographic image at a selected object image location of said plurality of candidate object image locations, comprising:

means for providing a radiograph of said object, including said plurality of candidate object image locations of said object, digitizer means having radiograph mapping means for applying said radiograph to said mapping means to map object locations, including said plurality of candidate object image locations, onto corresponding mapping means locations, means for indicating said selected object image location on said radiograph and transmitting to said processing means a location signal representative of the mapping means location corresponding to the indicated selected object image location, and said processing means having means for controlling said translating means to adjust the relative object to equipment position in accordance with the transmitted location signal.

11. The system of claim 10, further including exposure means under the control of said processing means, said exposure means having varying levels of radiation energy output for radiating the object, said processing means containing stored object density information representative of the density of said object at a plurality of object locations, said processing means further comprising means for controlling said exposure means to adjust the level of radiation energy output in accordance with the transmitted location signal and said stored object density information.

12. The method of claim 10, wherein said processing means includes means for controlling said translation means to provide predetermined pluridimensional patterns of adjustment of relative object to equipment position.

13. In a system for obtaining a tomographic image of an object having a plurality of candidate object image locations and a metering device having a known dimension, a method for locating a selected one of said plurality of candidate object image locations, comprising the steps of:

providing a radiograph of said object, including said plurality of candidate object image locations of said object and said metering device, applying said radiograph to mapping means of a digitizer to map object image locations, including said plurality of candidate object image locations and metering device image locations, onto corresponding mapping means locations, indicating selected object image locations on said radiograph, indicating selected metering device image locations on said radiograph wherein said selected metering device image locations are related to said known dimension, transmitting to said processing means location signals representative of the mapping means locations corresponding to the indicated object image location and the indicated metering device image locations, applying the transmitted indicated metering device image signals to said known dimension to determine a magnification factor, and applying said magnification factor to the indicated object image signals.

* * * * *